United States Patent [19]

Palumbo

[11] Patent Number: 6,068,924
[45] Date of Patent: *May 30, 2000

[54] ABSORBENT MATERIAL

[75] Inventor: Gianfranco Palumbo, Bad Homburg, Germany

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,298

[22] PCT Filed: Nov. 13, 1995

[86] PCT No.: PCT/US95/14677

§ 371 Date: May 12, 1997

§ 102(e) Date: May 12, 1997

[87] PCT Pub. No.: WO96/15163

PCT Pub. Date: May 23, 1996

[30] Foreign Application Priority Data

Nov. 10, 1994 [IT] Italy .................................. TO94A0890

[51] Int. Cl.$^7$ ....................................................... B32B 5/16
[52] U.S. Cl. .......................... 428/407; 428/402; 428/913; 604/367; 604/368
[58] Field of Search .................................. 428/411.1, 402, 428/407, 913; 604/367, 368

[56] References Cited

U.S. PATENT DOCUMENTS

| | | | |
|---|---|---|---|
| Re. 32,649 | 4/1988 | Brandt et al. | 604/368 |
| 2,586,883 | 2/1952 | Stroh | 260/43 |
| 3,558,744 | 1/1971 | Michaels et al. | 260/874 |
| 4,076,663 | 2/1978 | Masuda et al. | 260/17.4 |
| 4,489,180 | 12/1984 | Lundberg et al. | 523/175 |
| 4,666,983 | 5/1987 | Tsubakimoto et al. | 525/119 |
| 5,091,443 | 2/1992 | Karakelle et al. | 424/665 |
| 5,124,188 | 6/1992 | Roe et al. | 428/72 |
| 5,340,853 | 8/1994 | Chmelir et al. | 524/56 |

FOREIGN PATENT DOCUMENTS 57-045057 3/1982 Japan .............................. A41B 13/02

*Primary Examiner*—Helen L. Pezzuto
*Attorney, Agent, or Firm*—Edward J. Milbrada; Carl J. Roof; Steven W. Miller

[57] ABSTRACT

The invention provides a superabsorbent material which comprises a combination of (1) a cationic superabsorbent in which from 20 to 100% of the functional groups are in basic form, and (2) a cationic exchanger in which from 50 to 100% if the functional groups are in acid form. The combination is particularly effective as a superabsorbent for electrolyte containing solutions such as menses and urine.

18 Claims, No Drawings

6,068,924

ABSORBENT MATERIAL

The present invention relates to an absorbent material, more particularly a material of the type commonly referred to as a "superabsorbent".

The substances currently termed "superabsorbents" are typically slightly cross-linked hydrophilic polymers. The polymers may differ in their chemical nature but they share the property of being capable of absorbing and retaining even under moderate pressure amounts of aqueous fluids equivalent to many times their own weight. For example superabsorbents can typically absorb up to 100 times their own weight or even more of distilled water.

Superabsorbents have been suggested for use in many different industrial applications where advantage can be taken of their water absorbing and/or retaining properties and examples include agriculture, the building industry, the production of alkaline batteries and filters. However the primary field of application for superabsorbents is in the production of hygienic and/or sanitary products such as disposable sanitary napkins and disposable diapers either for children or for incontinent adults. In such hygienic and/or sanitary products, superabsorbents are used, generally in combination with cellulose fibres, to absorb body fluids such as menses or urine. However, the absorbent capacity of superabsorbents for body fluids is dramatically lower than for deionised water. It is generally believed that this effect results from the electrolyte content of body fluids and the effect is often referred to as "salt poisoning".

The water absorption and water retention characteristics of superabsorbents are due to the presence in the polymer structure of ionisable functional groups. These groups are usually carboxyl groups, a high proportion of which are in the salt form when the polymer is dry but which undergo dissociation and salvation upon contact with water. In the dissociated state, the polymer chain will have a series of functional groups attached to it which groups have the same electric charge and thus repel one another. This leads to expansion of the polymer structure which, in turn, permits further absorption of water molecules although this expansion is subject to the constraints provided by the cross-links in the polymer structure which must be sufficient to prevent dissolution of the polymer. It is assumed that the presence of a significant concentration of electrolytes in the water interferes with dissociation of the functional groups and leads to the "salt poisoning" effect. Although most commercial superabsorbents are anionic, it is equally possible to make cationic superabsorbents with the functional groups being, for example, quaternary ammonium groups. Such materials also need to be in salt form to act as superabsorbents and their performance is also affected by the salt-poisoning effect.

Attempts have been made to counteract the salt poisoning effect and improve the performance of superabsorbents in absorbing electrolyte containing liquids such as menses and urine. Thus Japanese Patent Application OPI No. 57-45, 057 discloses an absorbent which comprises a mixture of a superabsorbent such as a cross-linked polyacrylate with an ion exchange resin in powder or granular form. EP-A-0210756 relates to an absorbent structure comprising a superabsorbent and an anion exchanger, optionally together with a cation exchanger, wherein both ion exchangers are in fibrous form.

Combining a superabsorbent with an ion exchanger attempts to alleviate the salt poisoning effect by using the ion exchanger, generally as a combination of both an anion exchanger and a cation exchanger, to reduce the salt content of the liquid. The ion exchanger has no direct effect on the performance of the superabsorbent and it may not be possible to reduce the salt content sufficiently to have the desired effect on the overall absorption capacity of the combination.

In addition, besides being expensive, the ion exchanger has no absorbing effect itself and thus acts as a diluent to the superabsorbent.

An object of the present invention is to provide a superabsorbent with improved performance in the presence of electrolyte, for example in the case of menses or urine.

The present invention provides a superabsorbent material which comprises a combination of (1) a cationic superabsorbent in which from 20 to 100% of the functional groups are in basic form, and (2) a cation exchanger in which from 50 to 100% of the functional groups are in acid form.

The cationic superabsorbent preferably has from 50 to 100%, more preferably substantially 100% of the functional groups in basic form.

The cation exchanger preferably has substantially 100% of the functional groups in acid form.

It has now surprisingly been found according to the present invention that a combination of a cationic absorbent in basic form with a cation exchange in acid form is particularly effective as a superabsorbent in the case of electrolyte containing solutions, for example menses and urine.

Whilst not wishing to be bound by any particular theory, it is believed that there is a two fold effect when the superabsorbent material according to the invention is contacted with an electrolyte containing solution as follows:

(1) the cationic superabsorbent is converted from a non-absorbing form into the salt form in which it acts as a superabsorbent; and (2) conversion of the cationic superabsorbent into the salt forms has a de-ionising effect on the solution which is enhanced by the cation exchanger.

The functional groups in cationic superabsorbents are typically quaternary ammonium groups which are strong ion exchangers. Thus when the cationic superabsorbent is contacted with an electrolyte solution, for example a saline solution, it swells and the $OH^-$ ions from the superabsorbent are replaced in part with $Cl^-$ from solution and the pH of the solution will become strongly basic. However the presence of the cation exchange resin prevents the solution becoming strongly basic by displacing the equilibrium reaction in favour of the complete conversion of the cationic superabsorbent into the salt from. In so doing the sodium ions in solution are replaced by the cation exchange resin, chloride ions in solution are replaced by the cationic superabsorbent in base form thus causing substantial desalification of the saline solution and in turn improved absorbance of the superabsorbent.

This conversion of the anionic superabsorbent into the salt form on contact with an electrolyte containing solution and the effect of the cation exchanger in attaching sodium ions has a significant desalting effect on the solution thereby improving the performance of the superabsorbent by alleviating the salt-poisoning effect. In contrast with the use of an ion-exchange resin to desalt the solution in combination with a superabsorbent which is already in salt form (see Japanese Patent Application OPI No. 57-45057 and EP-A-0210756 referred to above) the cationic superabsorbent in basic form also has a de-salting effect on the solution. This allows a much greater de-salting effect to be achieved than by use of ion exchanger and superabsorbent in salt form. It should be noted that the effect of electrolyte in solution on the absorption capacity of a superabsorbent for that solution is not linear in that absorption capacity does not decrease regularly with increasing salt content. Accordingly over certain concentration ranges it is possible to bring about a relatively large increase in absorption capacity by effecting a relatively small reduction in salt content of the solution.

The cationic superabsorbent can be any material having superabsorbent properties in which the functional groups are cationic. Generally the functional groups are attached to a slightly cross-linked acrylic base polymer. For example, the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used. Starch and cellulose based polymers can also be used including hydroxypropyl cellulose, carboxymethyl cellulose and acrylic grafted starches. Particular base polymers include cross-linked polyacrylates, hydrolysed acrylonitrile grafted starch, starch polyacrylates, and isobutylene maleic anhydride copolymers. Particularly preferred base polymers are starch polyacrylates and cross-linked polyacrylates.

Examples of suitable cationic functional groups include quaternary ammonium groups or primary, secondary or tertiary amines which should be present in base form. For cellulose derivatives the degree of substitution (DS) of the derivative with the functional group is defined as the number of functional groups (generally quaternary ammonium groups) per anhydroglucose units of cellulose. The DS is generally from 0.1 to 1.5. In an analogous manner the DS for synthetic polymers may be defined as the number of functional groups per monomer or comonomer unit. The DS is generally 1, for example 1 quaternary ammonium group per monomer unit of polyacrylate. Preferred base polymers include polysaccharides and polymers based on dimethyldiallyl ammonium chloride.

According to one embodiment, the cationic superabsorbent can be a polysaccharide superabsorbent obtained by reacting a fibrous polysaccharide such as cellulose with an excess of a quaternary ammonium compound containing at least one group capable of reacting with polysaccharide hydroxyl groups and having a degree of substitution of 0.5 to 1.1. The quaternary ammonium compound may have the general formula:

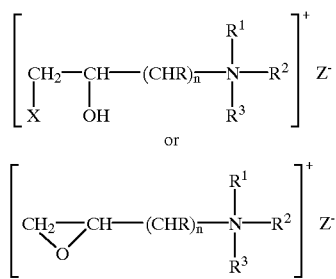

where n is an integer from 1 to 16; X is halogen; Z is an anion such as halide or hydroxyl; and R, $R^1$, $R^2$ and $R^3$, which may be the same or different, are each hydrogen, alkyl, hydroxyalkyl, alkenyl or aryl and $R^2$ may additionally represent a residue of formula

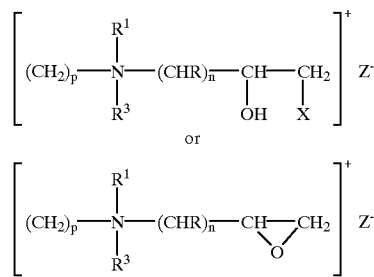

where p is an integer from 2 to 10 and n, R, $R^1$, $R^3$, X and Z have the meanings already defined. Cationic polysaccharide superabsorbents of this type are described in more detail in According to another embodiment the cationic superabsorbent may be a cross-linked cellulose based superabsorbent, in particular a fibrous cationic polysaccharide having superabsorbent characteristics, the polysaccharide being substituted by quaternary ammonium groups and having a ds of at least 0.5 and the polysaccharide being cross-linked to a sufficient extent that it remains insoluble in water. Superabsorbents of this type are described in more detail in our co-pending patent application Ser. No. 08/836, 297.

According to a further embodiment the cationic superabsorbent may be a water-swellable, water-insoluble polymer comprising units derived from a diallylic quaternary ammonium salt monomer, cross-linked by a suitable polyfunctional vinyl compound, characterised in that the polymer has been produced by radical polymerisation in an aqueous phase using a free radical catalyst. Superabsorbents of this type are described in more detail in our co-pending patent application Ser. No. 08/836,122.

Ion exchange is the reversible interchange of ions between a solid and liquid in which there is no permanent change in the structure of the solid, which is the ion-exchange material.

Ion exchange occurs in a variety of substances—e.g. silicates, phosphates, fluorides, humus, cellulose, wool, proteins, alumina, resins, lignin, cells, glass, barium sulphate, and silver chloride.

However, they are used for ion exchange materials that depend on properties other than the interchange of ions between liquid and solid phase. Ion exchange has been used on an industrial basis since 1910 with the introduction of water softening using natural and, later, synthetic zeolites.

The introduction of synthetic organic ion exchange resins in 1935 resulted from the synthesis of phenolic condensation products containing either sulfonic or amine groups which could be used for the reversible exchange of cations or anions.

Inorganic ion exchange materials include both the naturally occurring materials such as the mineral zeolites (e.g. cliptonite) the green sands and clay (e.g. the montmorillonite group), and synthetic products such as the gel zeolites, the hydrous oxides of polyvalent metals and the insoluble salts of polybaric acids with polyvalent metals.

Synthetic organic products include cation and anion ion exchange resins both of strong and weak type.

The weak acid, cation-exchange resins are based primarily on acrylic or methacrylic acid that has been crosslinked with a disfunctional monomer—e.g. DVB (divinylbenzene). Other weak acid resins have been made with phenolic of phosphonic functional groups.

The weak acid resin has a high affinity for the hydrogen ion and, thus is easily regenerated with strong acids. The property, however, limits the region in which salt splitting can occur to above pH 4.

The strong acid resins of commercial significance are sulfonated copolymer of styrene and DVB, sulfonic acid, sulfur trioxide, and chlorosulfonic acid have each been utilized for sulfonation.

These materials are characterized by their ability to exchange cations or split neutral salts and are useful across the entire pH range.

The cation exchanger is preferably a cation resin containing functional groups in acid form. Suitable functional groups include carboxylic or sulphonic acid groups.

The following cationic exchange resins may be used in the practise of the present invention:
Amberlite IR 120 which is a strong cation exchanger having sulfonic acid functionality which is available in $H^+$ form.
The total exchange capacity is 4.4 meq/g for the dry resin.
Amberlite IRC 76 which is a weak cation exchanger having carboxylic functionality which is available in acid form.
The total exchange capacity is 10 meq/g for dry resin.
Dowex 50W YZ which is a strong cation exchanger which is available in $H^+$ form having sulfonic acid functionality.
The total exchange capacity is 5 meq/g for dry resin.

In general the weight ratio cationic superabsorbent to cation exchanger is in the range 1:20 to 1:1 preferably 1:3 to 1:1 depending on molecular weight and ion exchange capacity.

The absorbent material according to the invention is particularly suitable for use in applications where it is desired to absorb electrolyte containing aqueous liquids. Examples of such liquids include in particular menses and urine and the absorbent material can be used as the filling in catamenials and diapers generally in admixture with a fibrous absorbent such as cellulose fluff. For this purpose the absorbent according to the invention can be present as granules or fibres.

The absorbent materials according to the invention show particularly good absorption of electrolyte containing aqueous liquids as is demonstrated below in the following examples by tests carried out using saline solution (1% NaCl) and synthetic urine.

Preparation—Cationic Superabsorbent based on crosslinked polydimethyl diallyl ammonium hydroxide called Fai 7 OH.
Preparation of Fai 7 OH
133 g of 60% aqueous solution of dimethyl diallyl ammonium chloride (DMAC available from fluka) were weighed into a 250 ml flask.
0.2 g of bisacrylamide (BAC available from fluka) were weighed separately into a 5 ml test tube and were dissolved in 2 ml of distilled water.
0.12 g of ammonium persulfate (free radical initiator) were dissolved in a 5 ml test tube in 2 ml of distilled water.
The monomer solution was disareated by vacuum using a vacuum pump.

Thereafter under continuous stirring the crosslinker solution and free radical initiator were added to the monomer solution, the temperature was adjusted to 60° C. by placing the flask in a thermostatic bath for four hours.

The solid product formed was cut using a spatula and transferred in 5 liter beaker containing 4 liters of distilled water, after two hours the swelled gel was filtered with a nonwoven tissue fabric filter. The gel was dried in a ventilated oven at 60° C. for 12 hours. 60 g of dried polymer was collected and called Fai 7 Cl. 20 g of Fai 7 Cl was placed in a 10 liter beaker and swelled by adding 4 liters of distilled water, under continuous stirring. When the polymer had swelled (after 2 hours) 500 ml of 0.01 M NaOH solution was added and after 30 minutes the gel was filtered using a nonwoven fabric tissue filter. These operations (alkalinization and filtration) were repeated until there were no chloride ions in the washing waters (chloride ions may be checked by $AgNO_3$ reaction). At this point the gel was washed with distilled water until there was no further evidence of the basic reaction in the washing waters.

Thereafter the gel was dried in an ventilated oven at 60° C. for 12 hours. 10 g of dried polymer was collected and was called Fai 7 OH.

EXAMPLES
1. Comparative Tests of Liquid Absorbtion

A test was performed to demonstrate that the use of both a cationic superabsorbent and a cation exchange resin may improve the absorbing performances of the cationic superabsorbent due to the desalting effect achieved by the ion exchange mixture.

A 1% NaCl solution (150 ml) was placed in contact with 2.23 g of the cation exchange resin IR120 ($H^+$) in a 250 ml beaker for 2 hours under continuous stirring. The sodium ions in the solution should be replaced by the $H^+$ ions from the resin. The solution was drawn up with a Pasteur pipette and dropped into another 250 ml beaker containing 0.11 g of Fai 7 OH under stirring; the addition is stopped when the gel swells no more. At this point the gel is placed into a nonwoven tissue "tea bag" small envelope and the absorbency after centrifugation at 60× g for 10 minutes was measured as follows:

$$A = (W\text{wet} - W\text{dry})/G$$

A=absorbency after centrifugation in g/g,
Wwet=weight of envelope containing the wet AGM after centrifugation in g,
Wdry=weight of the envelope containing the dry AGM in g,
G=weight of the AGM used in the test in g.

The test was also repeated using both Fai 9 $OH^-$ and Fai 9 $Cl^-$ individually without the cation exchange resin.
Results are as follows:

| | Amount | Absorption g/g (Tea-bag) | | Absorption g/g (Centrifuge) | |
|---|---|---|---|---|---|
| | (g) | $H_2O$ | 1% NaCl | $H_2O$ | 1% NaCl |
| Fai-7 $OH^-$ | 0.11 | 351 | 55 | 300 | 42 |
| Fai-7 $Cl^-$ | 0.11 | 340 | 54 | 290 | 43 |
| Fai-7 $OH^-$ + IR 120 ($H^+$) | 0.11 + 2.23 | — | 96.7 | — | 55 |

The above results show that the cationic superabsorbent in base form Fai-7 $OH^-$ and salt form (Fai-7 $Cl^-$) shows limited absorption in 1% NaCl solution as compared to deionised water. However in combination with the cationic exchanger in acid form IR120 ($H^+$) the material shows significantly increased absorption.

It should also be noted that 1% NaCl represents a stringent test of the superabsorbent. Studies in the literature show that the salt content of urine varies depending on a number of factors but 1% by weight represents the maximum likely to the encountered in practice.

What is claimed is:

1. A superabsorbent composition which comprises a combination of:
   1) a cationic superabsorbent having first functional groups in which from 20 to 100% of the first functional groups are in basic form; and
   2) a cation exchange resin having second functional groups in which from 50 to 100% of the second functional groups are in acid form;
   wherein the cationic superabsorbent and the cation exchange resin comprise separate chemical compounds whereby on exposure to an electrolyte solution comprising sodium ions and chloride ions, the cationic superabsorbent swells and releases hydroxyl ions due to ion exchange with the chloride ions and the cation exchange resin releases hydrogen ions due to ion exchange with the sodium ions whereby the hydroxyl ions and the hydrogen ions further reach to form water.

2. A superabsorbent material as claimed in claim 1 wherein the cationic superabsorbent has from 50 to 100%, of the functional groups in basic form and wherein the cation exchanger has substantially 100% of the functional groups in acid form.

3. A superabsorbent material as claimed in claim 1 wherein the functional groups in the cationic superabsorbent are primary, secondary or tertiary amines or quaternary ammonium groups.

4. A superabsorbent material as claimed in claim 3 wherein the functional groups are quaternary ammonium groups.

5. A superabsorbent as claimed in claim 1 wherein the first functional groups are attached to a backbone polymer selected from the group consisting of polyacrylamide, polyvinyl alcohol, ethylene maleic anhydride copolymer, polyvinyl ether, polyvinyl sulphonic acid, polyacrylic acid, polyvinylpyrolidone, polyvinylmorpholine, and copolymers thereof, a starch or cellulose based polymer.

6. A superabsorbent material as claimed in claim 5 wherein the starch or cellulose based polymer is hydroxypropyl cellulose, carboxymethyl cellulose or an acrylic grafted starch.

7. A superabsorbent as claimed in claim 6 wherein the base polymer is a cross-linked polyacrylate or an isobutylene maleic anhydride copolymer.

8. A superabsorbent as claimed in claim 7 wherein the base polymer is a starch polyacrylate or a cross-linked polyacrylate.

9. A superabsorbent material as claimed in claim 1 wherein the cationic superabsorbent is a polysaccharide superabsorbent obtained by reacting a fibrous polysaccharide with an excess of a quaternary ammonium compound containing at least one group capable of reacting with polysaccharide hydroxyl groups and having a degree of substitution of 0.5 to 1.1.

10. A superabsorbent material as claimed in claim 9 wherein thee quaternary ammonium compound has the general formula

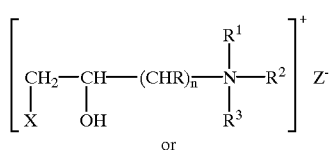

or

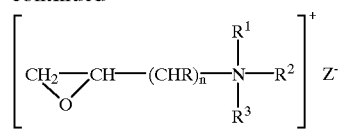

where n is an integer from 1 to 16; X is halogen; Z is an anion such as halide or hydroxyl; and R, $R^1$, $R^2$ and $R^3$, which may be the same or different, are each hydrogen, alkyl, hydroxyalkyl, alkenyl or aryl and $R^2$ may additionally represent a residue of formula

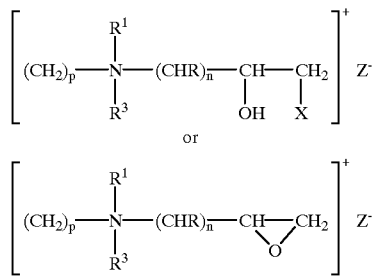

where p is an integer from 2 to 10 and n, R, $R^1$, $R^3$, X and Z have the meanings already defined.

11. A superabsorbent material as claimed in claim 1 wherein the cationic superabsorbent is a fibrous cationic polysaccharide having superabsorbent characteristics, the polysaccharide being substituted by quaternary ammonium groups and having a ds of at least 0.5 and the polysaccharide being cross-linked to a sufficient extent that it remains insoluble in water.

12. A superabsorbent material as claimed in claim 1 wherein the cationic superabsorbent is a water-swellable, water-insoluble polymer comprising units derived from a diallylic quaternary ammonium salt monomer, cross-linked by a suitable polyfunctional vinyl compound, characterised in that the polymer has been produced by cationic polymerisation in an aqueous phase using a free radical catalyst.

13. A superabsorbent material as claimed in claim 1 wherein the cation exchanger is a cation resin containing functional groups in acid form.

14. A superabsorbent material as claimed in claim 13 wherein the functional group is a carboxylic acid or sulphonic acid group.

15. A superabsorbent material as claimed in claim 1 wherein the weight ratio of cationic superabsorbent to cation exchanger is in the range of from 1:20 to 1:1.

16. A superabsorbent material as claimed in claim 15 wherein the weight ratio of cationic superabsorbent to cationic exchanger is from 1:3 to 1:1.

17. Use of a superabsorbent material as claimed in claim 1 for the absorbtion of electrolyte containing aqueous liquids.

18. A superabsorbent material as claimed in claim 2 wherein the cationic superabsorbent has substantially 100% of the functional groups in basic form.

* * * * *

UNITED STATES PATENT AND TRADEMARK OFFICE
CERTIFICATE OF CORRECTION

PATENT NO. : 6,068,924
DATED : May 30, 2000
INVENTOR(S) : Palumbo

It is certified that error appears in the above-identified patent and that said Letters Patent is hereby corrected as shown below:

Title page,
Item [30], Foreign Application Priority Data, please delete "TO94A0890" and insert therefor -- TO94A000890 --.
Item [57], ABSTRACT,
Line 5, please delete "if" and insert therefor -- of --.

Column 1,
Line 35, please delete "salvation" and insert therefor -- solvation --.

Column 6,
Line 53, please delete "Fai-7 $OH^-$ +" and insert therefor -- Fai-7 $OH^-$ --.
Line 53, please delete "0.11 + 2.23" and insert therefor -- 0.11 --.
Line 54, please delete "IR 120 ($H^+$)" and insert therefor -- + IR 120 ($H^+$) --.
Line 54, please insert -- +2.23 --.

Column 7,
Line 12, after "whereby" please insert -- , -- (a comma).
Line 18, please delete "reach" and insert therefor -- react --.
Line 20, after "100%", please delete "," (the comma).
Line 57, please delete "thee" and insert therefor -- the --.

Signed and Sealed this

Thirteenth Day of July, 2004

JON W. DUDAS
*Acting Director of the United States Patent and Trademark Office*